United States Patent
Schadow et al.

(10) Patent No.: US 10,418,828 B2
(45) Date of Patent: Sep. 17, 2019

(54) STORAGE SYSTEM

(71) Applicant: Robert Bosch GmbH, Stuttgart (DE)

(72) Inventors: Joachim Schadow, Stuttgart (DE); Manfred Lutz, Filderstadt (DE); Joern Stock, Leinfelden-Echterdingen (DE); Florian Esenwein, Leinfelden-Echterdingen (DE); Daniel Barth, Leinfelden-Echterdingen (DE); Cornelius Boeck, Kirchheim (DE); Joerg Maute, Sindelfingen (DE)

(73) Assignee: Robert Bosch GmbH, Stuttgart (DE)

( * ) Notice: Subject to any disclaimer, the term of this patent is extended or adjusted under 35 U.S.C. 154(b) by 243 days.

(21) Appl. No.: 15/504,279

(22) PCT Filed: Jul. 2, 2015

(86) PCT No.: PCT/EP2015/065141
§ 371 (c)(1),
(2) Date: Feb. 15, 2017

(87) PCT Pub. No.: WO2016/037722
PCT Pub. Date: Mar. 17, 2016

(65) Prior Publication Data
US 2017/0244262 A1    Aug. 24, 2017

(30) Foreign Application Priority Data
Sep. 9, 2014    (DE) .......................... 10 2014 217 965

(51) Int. Cl.
*H02J 7/00*    (2006.01)
*H02J 7/04*    (2006.01)
(Continued)

(52) U.S. Cl.
CPC ............ *H02J 7/0027* (2013.01); *A41D 1/002* (2013.01); *A41D 13/0002* (2013.01);
(Continued)

(58) Field of Classification Search
USPC .......................................................... 320/108
See application file for complete search history.

(56) References Cited

U.S. PATENT DOCUMENTS

| 8,791,600 B2* | 7/2014 | Soar ...................... H01F 27/365 307/104 |
| 2006/0087282 A1 | 4/2006 | Baarman et al. |
| 2014/0015336 A1* | 1/2014 | Weber ..................... H02J 5/005 307/104 |

FOREIGN PATENT DOCUMENTS

| DE | 202007004441 U1 | 7/2007 |
| EP | 2 365 698 A2 | 9/2011 |

(Continued)

OTHER PUBLICATIONS

International Search Report corresponding to PCT Application No. PCT/EP2015/065141, dated Sep. 2, 2015 (German and English language document) (7 pages).

*Primary Examiner* — Robert Grant
(74) *Attorney, Agent, or Firm* — Maginot, Moore & Beck LLP (57) ABSTRACT

A particular embodiment of a storage system includes at least one storage device. The storage device can store working clothing. The storage system further includes a wired and/or wireless charging device. The wired and/or wireless charging device can transmit electrical energy to an energy storage unit of the work clothing. The wired and/or wireless charging device can charge different work-clothing items of the work clothing. The work clothing can be disposed in the storage device. The storage system further includes a sensor device that can sense a characteristic variable of the work clothing.

13 Claims, 6 Drawing Sheets

(51) Int. Cl.
*A41D 1/00* (2018.01)
*H02J 7/02* (2016.01)
*A41D 13/00* (2006.01)
*A41D 19/015* (2006.01)
*A42B 3/00* (2006.01)
*A42B 3/04* (2006.01)
*A43B 3/00* (2006.01)
*A47B 61/04* (2006.01)
*A47B 81/00* (2006.01)
*A47B 97/00* (2006.01)
*A61F 9/02* (2006.01)
*H02J 50/10* (2016.01)

(52) U.S. Cl.
CPC ........ *A41D 19/01594* (2013.01); *A42B 3/006* (2013.01); *A42B 3/0406* (2013.01); *A43B 3/0005* (2013.01); *A47B 61/04* (2013.01); *A47B 81/00* (2013.01); *A47B 97/00* (2013.01); *A61F 9/029* (2013.01); *H02J 7/025* (2013.01); *H02J 7/042* (2013.01); *A47B 2220/0091* (2013.01); *H02J 50/10* (2016.02); *H02J 2007/0096* (2013.01)

(56) References Cited

FOREIGN PATENT DOCUMENTS

| | | |
|---|---|---|
| JP | 2004-33596 A | 2/2004 |
| JP | 2007-502100 A | 2/2007 |
| JP | 3167848 U | 5/2011 |
| JP | 2011-193719 A | 9/2011 |
| WO | 2010/093723 A1 | 8/2010 |

\* cited by examiner

STORAGE SYSTEM

This application is a 35 U.S.C. § 371 National Stage Application of PCT/EP2015/065141, filed on Jul. 2, 2015, which claims the benefit of priority to Serial. No. DE 10 2014 217 965.3, filed on Sep. 9, 2014 in Germany, the disclosures of which are incorporated herein by reference in their entirety.

BACKGROUND

DE 20 2007 004 441 U1 already describes a storage system which comprises a storage device for storing work clothing, a wireless charging device which is provided for transmitting electrical energy to an energy storage unit of the work clothing, and which comprises a sensor device for sensing a characteristic variable of the work clothing. A special work-clothing item is chargeable by means of the charging device of the known storage system.

SUMMARY

The disclosure is directed to a storage system, in particular a work-clothing storage system, comprising at least one storage device at least for storing work clothing, comprising at least one wired and/or wireless charging device which is provided for transmitting at least electrical energy to at least one energy storage unit of the work clothing, in particular in at least one state of the work clothing disposed on the storage device, and comprising at least one sensor device at least for sensing at least one characteristic variable of the work clothing.

It is proposed that the charging device is provided for charging different work-clothing items of the work clothing, which can be disposed on the storage device.

Particularly preferably, the storage system is designed as a work-clothing locker system. It is also conceivable, however, that the storage system has another design which appears reasonable to a person skilled in the art, such as, for example, a design as a wardrobe system, a chest-of-drawers system, a workshop wagon system, a shelving system, a vehicle-interior finishing storage system, or the like. The storage device is therefore preferably designed as a locker. It is also conceivable, however, that the storage device has another design which appears reasonable to a person skilled in the art. Particularly preferably, the storage system comprises a plurality of storage devices. In particular, the storage devices are connected to each other. The storage device is preferably designed to be closable. In this case, a storage compartment of the storage device is preferably closable. The storage device therefore preferably comprises at least one closure unit which comprises at least one movably mounted closure element. In particular, the closure unit is designed as a door unit. It is also conceivable, however, that the closure unit has another design which appears reasonable to a person skilled in the art. The closure element is preferably movably, in particular pivotably, mounted on a body of the storage device. Therefore, an inner space of the storage device, in which at least one storage unit of the storage device can be disposed, can be advantageously closed by means of the closure unit.

Advantageously, the storage device for storing work clothing comprises at least one storage unit which is designed as a clothes rail, a clothes hanger, a clothes hook, a shelf, a drawer a storage compartment and/or as a further storage unit which appears reasonable to a person skilled in the art, which is provided for accommodating work clothing or work-clothing items. The storage device is preferably additionally provided for accommodating work clothing for accommodating at least one machine tool accumulator device, at least one external unit, in particular a portable mobile communication device, such as, for example, a mobile phone, a smartphone, a tablet, etc., to at least one portable machine tool, or the like. "Provided" is intended to mean, in particular, specially designed and/or specially equipped. The wording that an element and/or a unit is provided for a certain function is intended to be understood to mean, in particular, that the element and/or the unit satisfy/satisfies and/or carry out/carries out this certain function in at least one application state and/or operating state.

In this case, a "wired charging device" is intended to mean, in particular, a charging device which transmits electrical energy by means of at least one charging cable to an element to be charged and/or to a unit to be charged. In this case, the term "wireless charging device" is intended to define, in particular, a charging device which contactlessly transmits electrical energy to an element to be charged and/or to a unit to be charged, in particular by means of an inductive, a capacitive, or an electromagnetic energy transmission. In this case, it is conceivable that the charging device comprises at least one inductive charging unit and, additionally, a cable charging unit. Therefore, depending on a design of a charging counterpart of the work clothing, a charging possibility could be reliably provided for differently designed charging counterparts of the work clothing.

The charging device is preferably designed as an inductive charging device. The charging device therefore preferably comprises at least one secondary coil unit for a transmission of electrical energy, wherein the work clothing, in particular all work-clothing items of the work clothing, comprises, in particular comprise, at least one primary coil unit for receiving the electrical energy. In this case, different nominal voltages are preferably usable for a transmission of electrical energy. The work clothing, in particular all work-clothing items of the work clothing, comprises or comprise preferably at least one energy storage unit which is designed as an accumulator. In this case, the energy storage unit preferably has a nominal voltage of 3.6 V. It is also conceivable, however, that the energy storage unit of the work clothing has another design and/or nominal voltage which appears reasonable to a person skilled in the art. Preferably, the charging device is provided, in addition for transmitting electrical energy to the work clothing, for transmitting electrical energy to at least one accumulator device, to at least one external unit, in particular a portable mobile communication device, such as, for example, a mobile phone, a smartphone, a tablet, etc., to at least one portable machine tool, or the like, in particular in a state disposed on the storage device and/or on the charging device. Furthermore, the charging device is preferably integrated into the storage device.

The sensor device is preferably provided for sensing at least one state-of-charge characteristic variable of the energy storage unit of the work clothing, in particular the energy storage unit of the particular work-clothing item of the work clothing. It is also conceivable that the sensor device is provided for sensing further characteristic values of the work clothing, which appear reasonable to a person skilled in the art, such as, for example, for sensing a correct arrangement of the work clothing on the storage device and/or on the charging device, or the like.

In this case, the expression "the charging device is provided for charging different work-clothing items of the work clothing, which can be disposed on the storage device" is intended to mean, in particular that the charging device is designed in such a way that at least electrical energy can be transmitted to different components of the work clothing by means of a single charging device, such as, for example, work gloves, a safety helmet, gloves, work pants, safety glasses, a belt, and/or other work-clothing items of the work clothing, which appear reasonable to a person skilled in the art. In this case, it is conceivable that all work-clothing items of the work clothing can be charged simultaneously by the charging device, in particular in a state of the different work-clothing items of the work clothing disposed on the storage device. By means of the design of the disclosure according to the disclosure, a storage system can be advantageously provided, which provides for a convenient possibility for charging different work-clothing items of the work clothing. A central storage system can therefore be advantageously implemented, which can be used for charging individual energy storage units of different work-clothing items of the work clothing. A storage system, which can be conveniently operated and loaded, can be advantageously implemented. A wearer of work clothing can therefore advantageously supply all of his work clothing with electrical energy using a single storage system, in particular in a state of the different work-clothing items of the work clothing disposed on the storage device.

In addition, it is provided that the storage device comprises at least one safety helmet storage unit, in which at least one work-clothing item of the work clothing, which is designed as a safety helmet, can be disposed, wherein at least one safety helmet charging unit of the charging device for charging at least one energy storage unit of the safety helmet is disposed on the safety helmet storage unit, in particular is integrated into the safety helmet storage unit. The safety helmet charging unit is preferably designed as a contactless safety helmet charging unit, in particular an inductive safety helmet charging unit. By means of the design according to the disclosure, a work-clothing item of the work clothing, which is designed as a safety helmet, can be conveniently stored and charged, which is advantageous.

Furthermore, it is provided that the storage device comprises at least one glove storage unit, in which at least one work-clothing item of the work clothing, which is designed as a pair of gloves, can be disposed, wherein at least one glove charging unit of the charging device for charging at least one energy storage unit of the pair of gloves is disposed on the glove storage unit, in particular is integrated into the glove storage unit. The glove charging unit is preferably designed as a contactless glove charging unit, in particular an inductive glove charging unit. By means of the design according to the disclosure, a work-clothing item of the work clothing, which is designed as a pair of gloves, can be conveniently stored and charged, which is advantageous.

It is also provided that the storage device comprises at least one work shoe storage unit, in which at least one work-clothing item of the work clothing, which is designed as a pair of work shoes, can be disposed, wherein at least one work shoe charging unit of the charging device for charging at least one energy storage unit of the pair of work shoes is disposed on the work shoe storage unit, in particular is integrated into the work shoe storage unit. The work shoe charging unit is preferably designed as a contactless work shoe charging unit, in particular an inductive work shoe charging unit. Furthermore, it is conceivable that the storage device comprises further storage units, which appear reasonable to a person skilled in the art, such as, for example, a work belt storage unit, a work sock storage unit, a work undergarment storage unit, wherein disposed on each of the particular further storage units is a charging unit of the charging device for charging an energy storage unit of a corresponding work-clothing item. By means of the design according to the disclosure, a work-clothing item of the work clothing, which is designed as a pair of work shoes, can be conveniently stored and charged, which is advantageous.

In addition, it is provided that the storage device comprises at least one safety glasses storage unit, in which at least one work-clothing item of the work clothing, which is designed as safety glasses, can be disposed, wherein at least one safety glasses charging unit of the charging device for supplying energy at least to an energy storage unit of the safety glasses is disposed on the safety glasses storage unit, in particular is integrated into the safety glasses storage unit. The safety glasses charging unit is preferably designed as a contactless safety glasses charging unit, in particular an inductive safety glasses charging unit. By means of the design according to the disclosure, a work-clothing item of the work clothing, which is designed as safety glasses, can be conveniently stored and charged, which is advantageous.

Advantageously, it is provided that the charging device is provided for charging at least one machine tool accumulator device and/or at least one energy storage unit of an external unit, in particular in a state of the machine tool accumulator device and/or of the external unit disposed on the storage device. Preferably, the charging device comprises, for this purpose, at least one machine tool accumulator unit and/or a charging unit for charging the external unit. In addition, the storage device comprises preferably at least one machine tool storage unit and/or a storage unit for storing the external unit. Preferably, the machine tool accumulator charging unit and/or the charging unit for charging the external unit are/is integrated into the machine tool storage unit and/or into the storage unit for storing the external unit. The external unit is preferably designed as a portable mobile communication device, such as, for example, a mobile phone, a smartphone, a tablet, or the like. It is also conceivable, however, that the external unit has a different design which appears reasonable to a person skilled in the art. By means of the design according to the disclosure, a broad range of applications of the storage system can be advantageously implemented.

Furthermore, it is provided that the storage system comprises at least one communication device at least for exchanging electronic data with the work clothing, in particular in at least one state of the work clothing disposed on the storage device. The communication device is preferably designed as a wireless communication device. In this case, the communication device can be designed as a WLAN communication device, a Bluetooth communication device, a radio communication device, an RFID communication device, an NFC communication device, an infrared communication device, a mobile network communication device, as a Zigbee communication device, or the like. Particularly preferably, the communication device is provided for bidirectional data transmission. In one alternative embodiment, the communication device is designed as a wired communication device, such as, for example, a LAN communication device, a USB communication device, a power-line communication device, a CAN bus communication device, an Ethernet communication device, a twisted pair cable communication device (CAT5 or CAT6), or the like. It is also conceivable, however, that the communication device is provided for wireless and wired communication, alternatively to being provided for wireless or wired communication. An exchange of electronic data for monitoring the work clothing can be advantageously made possible by means of the design according to the disclosure.

In addition, it is provided that electronic data can be exchanged between the work clothing and an external unit by means of the communication device. The external unit can be designed as a smartphone, a personal computer, a laptop, a netbook, a tablet, a corporate mainframe computer, a portable machine tool, an output unit, such as, for example, a loudspeaker, or as another external unit which appears reasonable to a person skilled in the art. In an embodiment as a smartphone, a personal computer, a laptop, a netbook, or a tablet, preferably an app is provided for communication with the communication device. It is also conceivable, however, that the external unit is designed as an external, transportable control unit, as a fixedly installed control unit at a workstation of an operator, as a synchronization unit of a usage location, which is fixedly installed in a room and can be controlled from a central office in respect of, for example, company requirements/safety regulations, or as a further centralized or decentralized control unit, input station and/or centralized or decentralized terminal which appears reasonable to a person skilled in the art. Advantageously, a synchronization of electronic data can be therefore made possible. If a presence of a work-clothing item of the work clothing is detected, for example, by means of a sensor element of the sensor unit, a connection between the communication device and the external unit is at least partially automatically established. Settings stored in the external unit are therefore preferably directly transferrable to the work-clothing item of the work clothing and/or from the work-clothing item of the work clothing to the external unit. These can be individualized settings or these can be company requirements. An individualized setting of characteristic quantities of the work clothing can be made possible, advantageously, by means of the design according to the disclosure. In addition, a centralized control of functions of the work clothing and/or of the storage system can be advantageously made possible. Furthermore, a software update or a backup of electronic data can advantageously take place during a charging process. In this case, it is conceivable that opening the storage system can be prevented for as long as a data transmission has not yet been completed and/or a charging process has not ended, in order to avoid faults.

In addition, it is provided that electronic data which define a usage duration and/or a degradation of the work clothing can be exchanged by means of the communication device, wherein the usage duration and/or the degradation can be sensed by at least one sensor unit of the work clothing and/or by the sensor device. Therefore, a replacement of the work clothing can be advantageously initiated after a predefined maximum service life has been reached and/or after a maximum degradation has been reached. As a result, it can be advantageously ensured that the work clothing provides for a reliable protective function for a wearer.

Furthermore, it is provided that electronic data which define a user-specific characteristic variable of a wearer of the work clothing can be exchanged by means of the communication device, wherein the user-specific characteristic variable can be sensed by at least one sensor unit of the work clothing. In this case, a "user-specific characteristic variable" is intended to mean, in particular, a characteristic variable which defines at least one vital value of a wearer of the work clothing, which is dependent on a behavior and/or on a wearing duration of a wearer of the work clothing. The user-specific characteristic variable can be designed, in this case, as a user-specific work clothing load, such as, for example, a noise impact and/or a vibration load, as a pulse of a wearer of the work clothing, as a body temperature of a wearer of the work clothing, as a tiredness characteristic variable of a wearer of the work clothing, as a support orientation characteristic variable, as a work clothing movement characteristic variable, or as another user-specific characteristic variable which appears reasonable to a person skilled in the art. By means of the design according to the disclosure, additional compensation of a wearer, which is dependent on work time, can be advantageously implemented. For example, a vibration (vibration dose) absorbed by a wearer of the work clothing during a work shift or during work time can be advantageously communicated to a centralized service point via the communication device and, therefore, suitable additional compensation can be paid to the wearer.

In addition, it is provided that the storage system comprises at least one control and/or regulating device which is provided for setting at least one characteristic variable of the work clothing depending on an individualized user input and/or depending on electronic data exchanged by means of the communication device. A "control and/or regulating device" is intended to mean, in particular, a device having at least one set of control electronics. "Control electronics" is intended to mean, in particular, a unit comprising a processor unit and comprising a memory unit, and comprising an operating program stored in the memory unit. By means of the embodiment according to the disclosure, an adaptation of settings of the work clothing to individual needs of a wearer can advantageously take place, in particular during a charging process of the work clothing. In this case, a setting at least of one characteristic variable of the work clothing can advantageously take place from a centralized service point and/or a wearer of the work clothing can advantageously implement a setting of the at least one characteristic variable by interacting with the communication device and an external unit.

In addition, it is provided that the storage system comprises at least one drying and/or cleaning device which is provided for carrying out a drying and/or cleaning process of the work clothing depending on at least one characteristic variable sensed by means of the sensor device and/or depending on electronic data exchanged by means of the communication device. Therefore, an at least partially automatic drying and/or cleaning process can be advantageously achieved. A reliable usability of the work clothing can therefore take place.

Furthermore, it is provided that the storage system comprises at least one output device for outputting information regarding at least one state of the work clothing. The output device in this case can be designed to be optical, haptic and/or acoustic. Preferably, the output device is designed at least as an optical output device. By means of the design according to the disclosure, a status can be advantageously communicated to a wearer, whereby the wearer, therefore, can be advantageously informed about a status of the work clothing, in particular in a state of the work clothing disposed on the storage device.

In one alternative design of the storage system, it is provided that at least the storage system is designed to be mobile or is integrated in a mobile unit. In this case, it is conceivable that the storage device comprises at least one mobility unit, by means of which the storage device is movable. The mobility unit can be designed, in this case, as a roller unit, a chain unit, an air cushion unit, a magnetic unit, or as another mobility unit which appears reasonable to a person skilled in the art. The mobile unit is preferably designed as a transport vehicle, such as, for example, a passenger car, a commercial vehicle, or a truck, into which the storage device is integrated. Particularly preferably, all devices of the storage system are designed to be mobile or are integrated in a mobile unit. The entire storage system is therefore preferably designed to be mobile or is integrated in a mobile unit. By means of the design according to the disclosure, a high degree of flexibility with respect to a usage site of the storage system can be advantageously achieved.

In addition, a charging device, in particular for a storage system according to the disclosure, is provided, wherein the charging device is at least provided for transmitting electrical energy, in particular contactlessly, to at least one energy storage unit of a work clothing. The charging device is preferably provided for transmitting electrical energy, in particular contactlessly, to different work-clothing items of the work clothing. A charging device having a broad range of applications can be therefore advantageously provided.

The storage system according to the disclosure and/or the charging device according to the disclosure should not be limited, in this case, to the above-described application and embodiment. In particular, the storage system according to the disclosure and/or the charging device according to the disclosure can have a number of individual elements, components, and units which deviates from a number mentioned herein, in order to operate in a manner described herein. In addition, in respect of the value ranges indicated in this disclosure, values lying within the stated limits should also be considered to be disclosed and to be usable in any manner.

BRIEF DESCRIPTION OF THE DRAWINGS

Further advantages result from the following description of the drawing. The drawing shows a representation of three exemplary embodiments of the disclosure. The drawing, the description, and the claims contain numerous features in combination. A person skilled in the art will advantageously also consider the features individually and group them into further reasonable combinations.

In the drawings.

DETAILED DESCRIPTION

Figure 1:
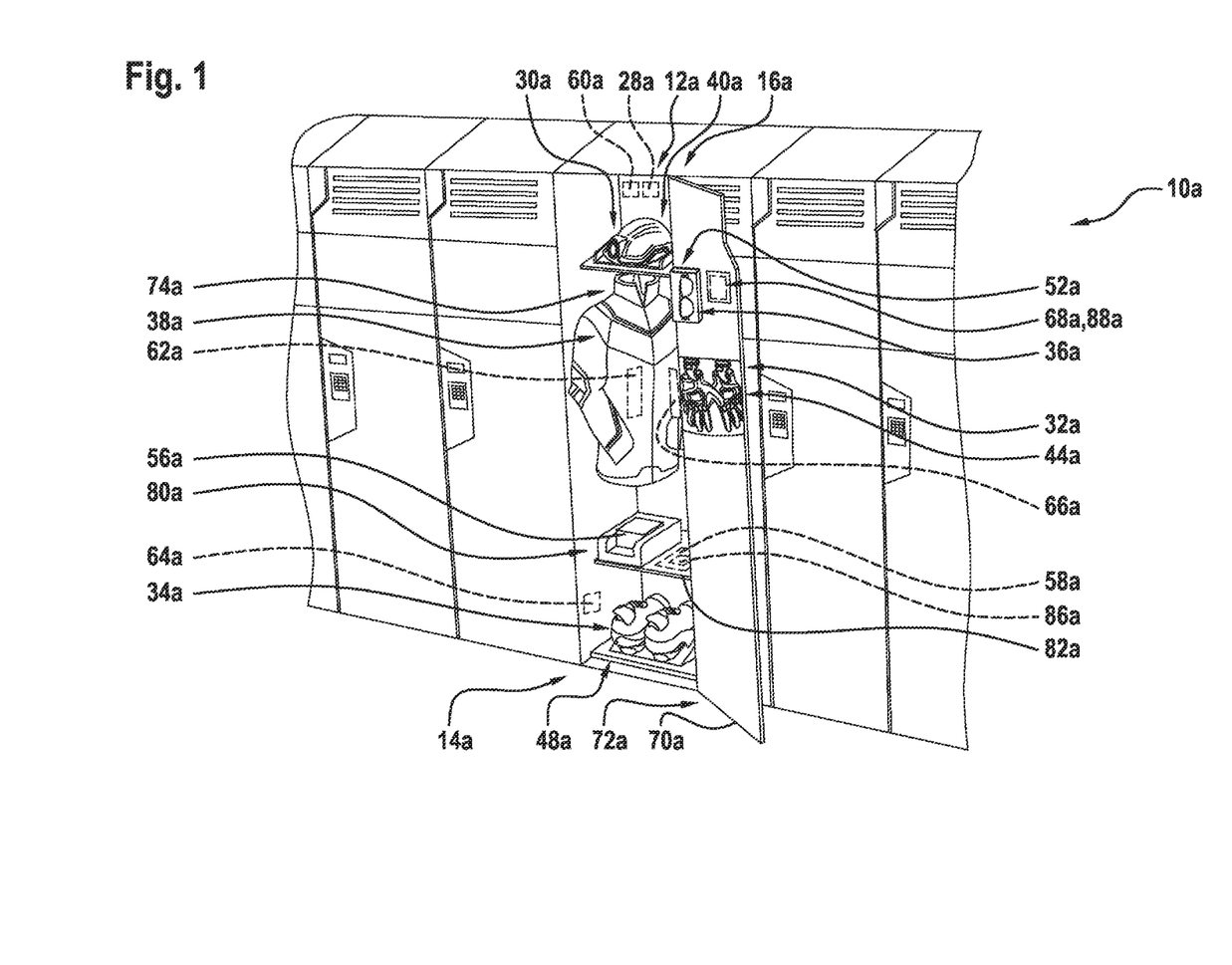
FIG. 1 shows a schematic representation of a storage system according to the disclosure comprising a plurality of interconnected storage devices.

FIG. 1 shows a storage system 10a designed as a work clothing storage system. The storage system 10a comprises at least one storage device 12a at least for storing work clothing 14a. In this case, the storage device 12a is designed as a locker. In all, the storage system 10a comprises a plurality of storage devices 12a which have an at least essentially similar design. The storage system 10a is therefore designed as a locker system. In the storage system 10a represented in FIG. 1, the storage devices 12a are directly connected to each other. It is also conceivable, however, that the storage devices 12a are disposed spaced from each other, wherein a communication of the storage devices 12a, which are disposed spaced from each other, is conceivable.

Furthermore, the storage system 10a comprises at least one wired and/or wireless charging device 16a which is provided for transmitting at least electrical energy to at least one energy storage unit 18a, 20a, 22a, 24a, 26a of the work clothing 14a, and at least one sensor device 28a at least for sensing at least one characteristic variable of the work clothing 14a. The sensor device 28a is provided, in particular, for sensing at least one characteristic variable of the work clothing 14a in a state of the work clothing 14a disposed on the storage device 12a. The charging device 16a is provided for transmitting at least electrical energy to at least one energy storage unit 18a, 20a, 22a, 24a, 26a of the work clothing 14a in a state of the work clothing 14a disposed on the storage device 12a. The charging device 16a is integrated into the storage device 12a. The storage device 12a is provided for storing different work-clothing items 30a, 32a, 34a, 36a, 38a of the work clothing 14a. The charging device 16a is therefore provided for charging different work-clothing items 30a, 32a, 34a, 36a, 38a of the work clothing 14a, which can be disposed on the storage device 12a. In this case, the charging device 16a is designed, in particular, as an inductive charging device, wherein the charging device 16a comprises a secondary coil unit and the work clothing 14a, in particular the individual work-clothing items 30a, 32a, 34a, 36a, 38a of the work clothing 14a, comprises or comprise a primary coil unit. The charging device 16a can also be designed independently of the storage system 10a and can be used independently. In this case, the charging device 16a is provided at least for transmitting electrical energy, in particular contactlessly, to at least one energy storage unit 18a, 20a, 22a, 24a, 26a of work clothing 14a.

Figure 2:
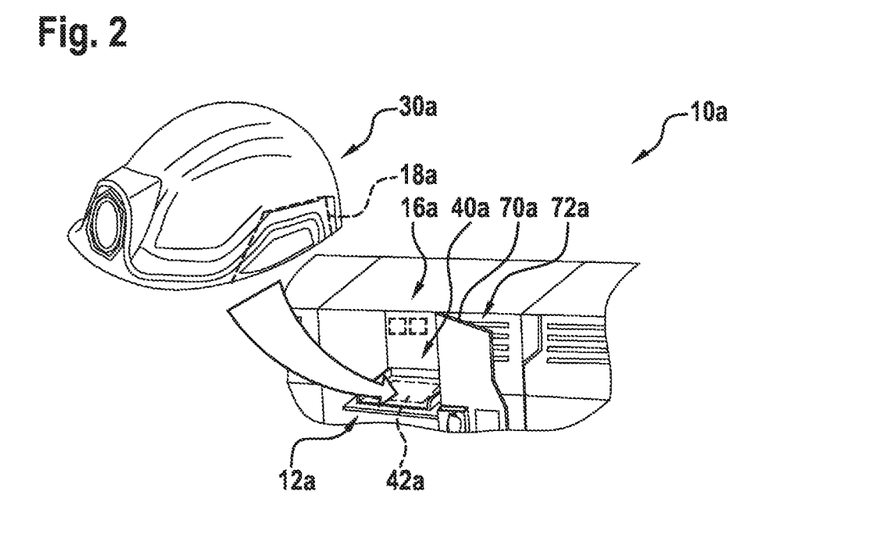
FIG. 2 shows a schematic representation of a detailed view of a safety helmet storage unit of one of the storage devices of the storage system according to the disclosure.

The storage device 12a comprises at least one safety helmet storage unit 40a, in which at least one work-clothing item 30a of the work clothing 14a, which is designed as a safety helmet, can be disposed, wherein at least one safety helmet charging unit 42a of the charging device 16a is disposed on the safety helmet storage unit 40a for charging at least one energy storage unit 18a of the safety helmet (FIGS. 1 and 2). The energy storage unit 18a of the safety helmet is provided for supplying energy to electrical and/or electronic components of the safety helmet, such as, for example, for supplying energy to a lighting unit of the safety helmet, a sensor unit of the safety helmet, a data transmission unit of the safety helmet, an output unit of the safety helmet, an active hearing-protection unit of the safety helmet, a heating unit of the safety helmet, or the like. The safety helmet storage unit 40a is provided as a safety helmet storage shell, in which the safety helmet can be disposed. In this case, the safety helmet storage unit 40a is disposed in an upper storage compartment of the storage device 12a. It is also conceivable, however, that the safety helmet storage unit 40a has another design and/or arrangement which appears reasonable to a person skilled in the art. The safety helmet charging unit 42a is designed as an inductive safety helmet charging unit. In this case, the safety helmet comprises a charging unit corresponding to the safety helmet charging unit 42a. In a state of the safety helmet disposed on the safety helmet storage unit 40a, the energy storage unit 18a of the safety helmet is therefore chargeable by means of an inductive charging process. In this case, the safety helmet charging unit 42a and the charging unit of the safety helmet can be connected to each other, in particular contactlessly connected to each other, such as, for example, inductively connected to each other, after the safety helmet has been disposed on the safety helmet storage unit 40a. It is also conceivable, however, that the safety helmet charging unit 42a is designed as a contact charging unit and the safety helmet comprises a counter-contact charging unit, which are designed so as to correspond to each other.

Figure 3:
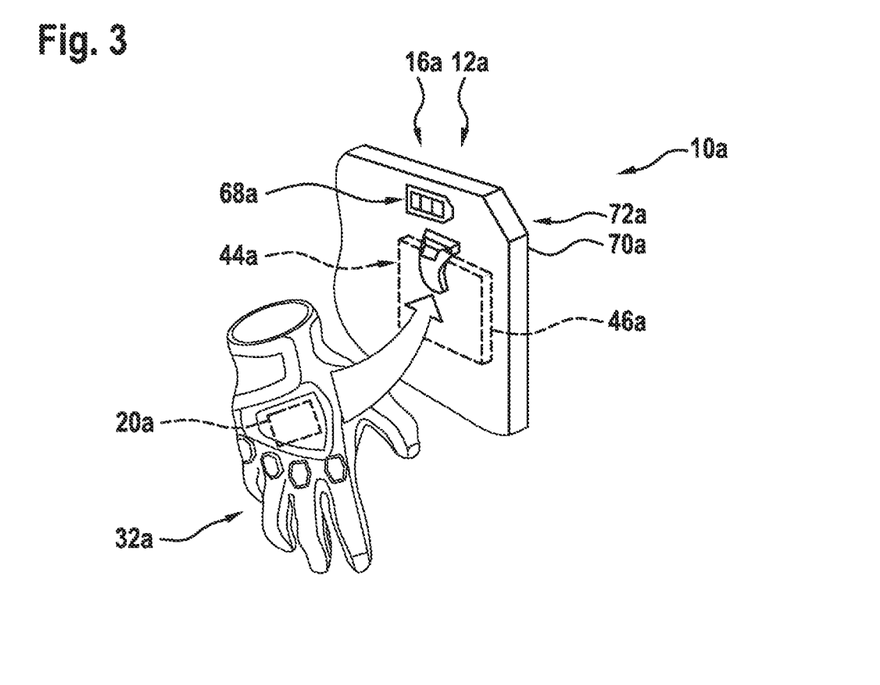
FIG. 3 shows a schematic representation of a detailed view of a glove storage unit of one of the storage devices of the storage system according to the disclosure.

In addition, the storage device 12a comprises at least one glove storage unit 44a, in which at least one work-clothing item 32a of the work clothing 14a, which is designed as a pair of gloves, can be disposed, wherein at least one glove charging unit 46a of the charging device 16a is disposed on the glove storage unit 44a for charging at least one energy storage unit 20a of the pair of gloves (FIGS. 1 and 3). The energy storage unit 20a of the pair of gloves is provided for supplying energy to electrical and/or electronic components of the pair of gloves, such as, for example, supplying energy to a lighting unit of the pair of gloves, a sensor unit of the pair of gloves, a data transmission unit of the pair of gloves, a heating unit of the pair of gloves, or the like. The glove storage unit 44a is designed as a clamping and/or snap-in unit, by means of which the pair of gloves can be disposed on the storage device 12a. In this case, one glove of the pair of gloves can be disposed in each case on, in particular fixedly clamped to and/or snapped into, the storage device 12a by means of a clamping and/or snap-in element of the glove storage unit 44a. The glove storage unit 44a is disposed on a closure element 70a of a closure unit 72a of the storage device 12a, in particular on an inner side of the closure element 70a facing a storage space of the storage device 12a in a closed state of the storage device 12a. The closure element 70a is designed as a pivotably mounted locker door which is provided for closing the storage space of the storage device 12a. It is also conceivable, however, that the glove storage unit 44a has another design and/or arrangement which appears reasonable to a person skilled in the art, such as, for example, a design as a magnetic holding unit, or the like. The glove charging unit 46a is designed as an inductive glove charging unit.

The pair of gloves, in particular each glove of the pair of gloves, comprises a charging unit which corresponds to the glove charging unit 46a. In a state of the pair of gloves disposed on the glove storage unit 44a, the energy storage unit 20a of the pair of gloves is therefore chargeable by means of an inductive charging process. In this case, the glove charging unit 46a and the charging unit of the pair of gloves can be connected to each other, in particular contactlessly connected to each other, such as, for example, inductively connected to each other, after the pair of gloves has been disposed on the glove storage unit 44a. It is also conceivable, however, that the glove charging unit 46a is designed as a contact charging unit and the pair of gloves comprises a counter-contact charging unit, which are designed so as to correspond to each other.

Figure 4:
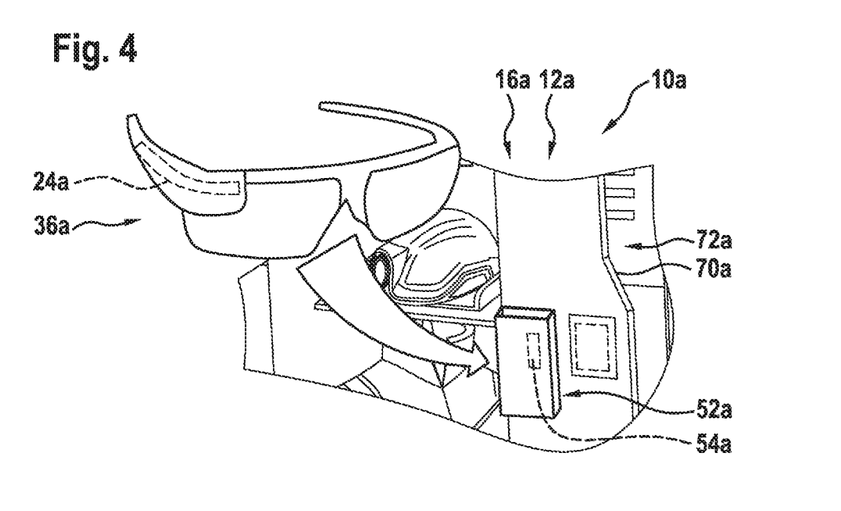
FIG. 4 shows a schematic representation of a detailed view of a safety glasses storage unit of one of the storage devices of the storage system according to the disclosure.

Furthermore, the storage device 12a comprises at least one safety glasses storage unit 52a, in which at least one work-clothing item 36a of the work clothing 14a, which is designed as safety glasses, can be disposed, wherein at least one safety glasses charging unit 54a of the charging device 16a is disposed on the safety glasses storage unit 52a for charging at least one energy storage unit 24a of the safety glasses (FIGS. 1 and 4). The energy storage unit 24a of the safety glasses is provided for supplying energy to electrical and/or electronic components of the safety glasses, such as, for example, supplying energy to a lighting unit of the safety glasses, a sensor unit of the safety glasses, a data transmission unit of the safety glasses, an output unit of the safety glasses, or the like. The safety glasses storage unit 52a is designed as a safety glasses storage compartment, by means of which the safety glasses can be disposed on the storage device 12a. In this case, the safety glasses storage unit 52a is disposed on the closure element 70a, in particular on the inner side of the closure element 70a facing the storage space in a closed state of the storage device 12a. It is also conceivable, however, that the safety glasses storage unit 52a has another design and/or arrangement which appears reasonable to a person skilled in the art. The safety glasses charging unit 54a is designed as an inductive safety glasses charging unit. In this case, the safety glasses comprise a charging unit corresponding to the safety glasses charging unit 54a. In a state of the safety glasses disposed on the safety glasses storage unit 52a, the energy storage unit 24a of the safety glasses is therefore chargeable by means of an inductive charging process. In this case, the safety glasses charging unit 54a and the charging unit of the safety glasses can be connected to each other, in particular contactlessly connected to each other, such as, for example, inductively connected to each other, after the safety glasses have been disposed on the safety glasses storage unit 52a. It is also conceivable, however, that the safety glasses charging unit 54a is designed as a contact charging unit and the safety glasses comprise a counter-contact charging unit, which are designed so as to correspond to each other.

Figure 5:
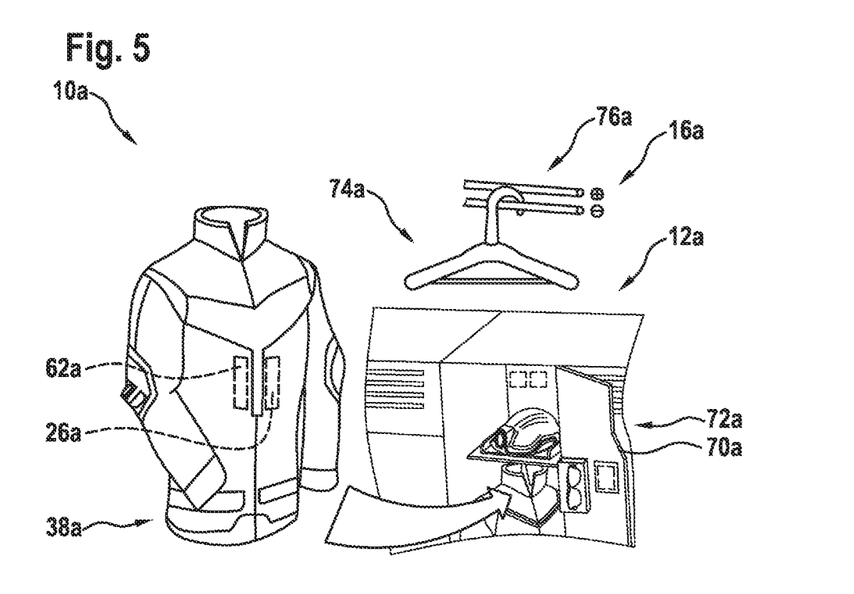
FIG. 5 shows a schematic representation of a detailed view of a work jacket storage unit of one of the storage devices of the storage system according to the disclosure.

In addition, the storage device 12a comprises at least one work jacket storage unit 74a, on which at least one work-clothing item 38a of the work clothing 14a, which is designed as work jacket, can be disposed, wherein at least one work jacket charging unit 76a of the charging device 16a is disposed on the work jacket storage unit 74a for charging at least one energy storage unit 26a of the work jacket (FIGS. 1 and 5). The energy storage unit 26a of the work jacket is provided for supplying energy to electrical and/or electronic components of the work jacket, such as, for example, supplying energy to a lighting unit of the work jacket, a sensor unit 62a of the work jacket, a data transmission unit of the work jacket, an output unit of the work jacket, or the like. The work jacket storage unit 74a is designed as a clothes hanger- and clothes rail-unit, by means of which the work jacket can be disposed on the storage device 12a. It is also conceivable that the work jacket storage unit 74a is provided, alternatively or additionally, for storing a work-clothing item (not shown here in greater detail) of the work clothing 14a, which is designed as work pants or a work vest, and/or the work jacket charging unit 76a is provided for charging an energy storage unit of a work-clothing item (not shown here in greater detail) of the work clothing 14a, which is designed as work pants or a work vest. The work jacket storage unit 74a is disposed in the storage space of the storage device 12a. It is also conceivable, however, that the work jacket storage unit 74a has another design and/or arrangement which appears reasonable to a person skilled in the art. The work jacket charging unit 76a is designed as an inductive work jacket charging unit. In this case, the work jacket comprises a charging unit corresponding to the work jacket charging unit 76a. In a state of the work jacket disposed on the work jacket storage unit 74a, the energy storage unit 26a of the work jacket is therefore chargeable by means of an inductive charging process. In this case, the work jacket charging unit 76a and the charging unit of the work jacket can be connected to each other, in particular contactlessly connected to each other, such as, for example, inductively connected to each other, after the work jacket has been disposed on the work jacket storage unit 74a. It is also conceivable, however, that the work jacket charging unit 76a is designed as a contact charging unit and the work jacket comprises a counter-contact charging unit, which are designed so as to correspond to each other.

Figure 6:
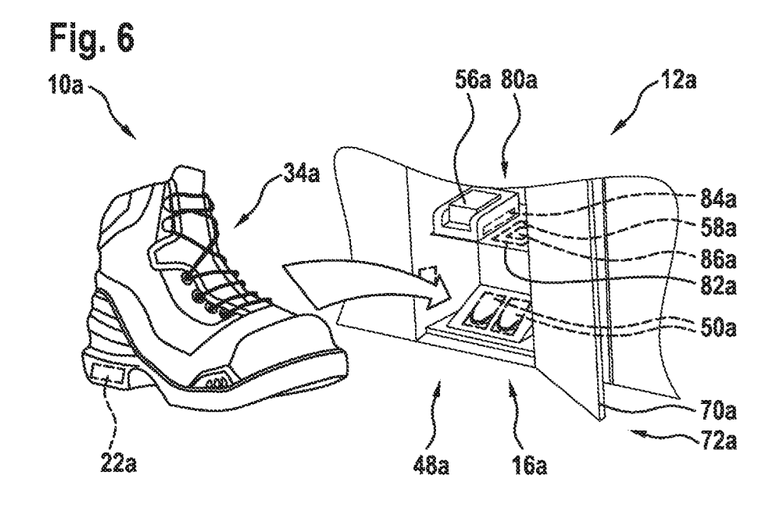
FIG. 6 shows a schematic representation of a detailed view of a work shoe storage unit of one of the storage devices of the storage system according to the disclosure.
Figure 7:
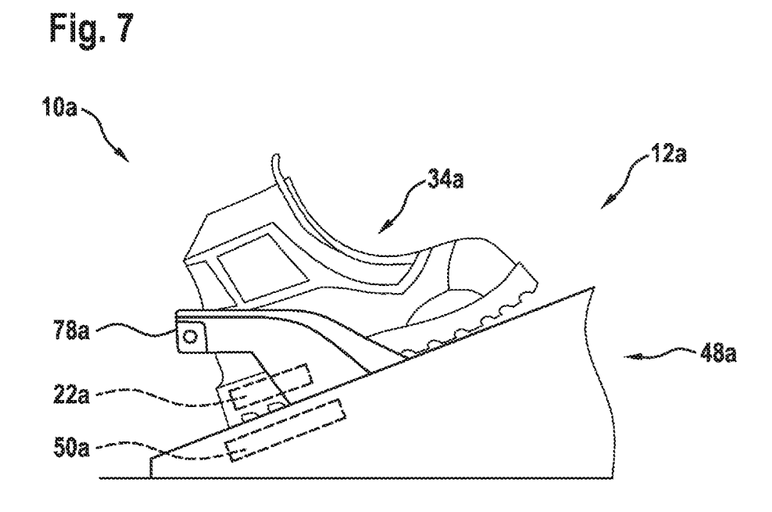
FIG. 7 shows a schematic representation of a further detailed view of the work shoe storage unit of one of the storage devices of the storage system according to the disclosure.

In addition, the storage device 12a comprises at least one work shoe storage unit 48a, in which at least one work-clothing item 34a of the work clothing 14a, which is designed as a pair of work shoes, can be disposed, wherein at least one work shoe charging unit 50a of the charging device 16a is disposed on the work shoe storage unit 48a for charging at least one energy storage unit 22a of the pair of work shoes (FIGS. 1, 6 and 7). The energy storage unit 22a of the pair of work shoes is provided for supplying energy to electrical and/or electronic components of the pair of work shoes, such as, for example, supplying energy to a lighting unit of the pair of work shoes, a sensor unit of the pair of work shoes, a data transmission unit of the pair of work shoes, an output unit of the pair of work shoes, or the like. The work shoe storage unit 48a is designed as a work shoe storage compartment, in which the pair of work shoes can be disposed. The work shoe storage unit 48a comprises at least one stirrup-shaped work shoe holding element 78a, against which one work shoe of the pair of work shoes rests in a state disposed on the work shoe storage unit 48a. In all, the work shoe storage unit 48a comprises at least two stirrup-shaped work shoe holding elements 78a, wherein one work shoe of the pair of work shoes, in each case, rests against one of the stirrup-shaped work shoe holding elements 78a, in particular via a heel region of the particular work shoe, in a state disposed on the work shoe storage unit 48a. In this case, the work shoe storage unit 48a is disposed in the storage space of the storage device 12a. It is also conceivable, however, that the work shoe storage unit 48a has another design and/or arrangement which appears reasonable to a person skilled in the art.

The work shoe charging unit 50a is designed as an inductive work shoe charging unit. In this case, the pair of work shoes, in particular each work shoe of the pair of work shoes, comprises a charging unit which corresponds to the work shoe charging unit 50a. In a state of the pair of work shoes disposed on the work shoe storage unit 48a, the energy storage unit 22a of the pair of work shoes is therefore chargeable by means of an inductive charging process. The work shoe charging unit 50a is disposed, in this case, on the stirrup-shaped work shoe holding element 78a or in a base plate of the work shoe charging unit 50a and/or of the work shoe storage unit 48a. The work shoe charging unit 50a and the charging unit of the pair of work shoes can be connected to each other, in particular contactlessly connected to each other, such as, for example, inductively connected to each other, after the pair of work shoes has been disposed on the work shoe storage unit 48a. It is also conceivable, however, that the work shoe charging unit 50a is designed as a contact charging unit and the pair of work shoes comprises a counter-contact charging unit, which are designed so as to correspond to each other.

Furthermore, the charging device 16a is provided for charging at least one machine tool accumulator device 56a and/or at least one energy storage unit of an external unit 58a. The charging device 16a is provided for charging at least one machine tool accumulator device 56a and/or at least one energy storage unit of an external unit 58a in a state disposed on the storage device 12a. For this purpose, the charging device 16a comprises at least one machine tool accumulator charging unit 84a and/or at least one charging unit 86a for charging the external unit 58a. In addition, the storage device 12a comprises at least one machine tool accumulator receiving unit 80a and/or at least one storage unit 82a for storing the external unit 58a. The machine tool accumulator charging unit 84a is disposed on the machine tool accumulator receiving unit 80a. The charging unit 86a for charging the external unit 58a is disposed on the storage unit 82a for storing the external unit 58a. In this case, the machine tool accumulator charging unit 84a and/or the charging unit 86a for charging the external unit 58a are/is designed as an inductive charging unit. It is also conceivable, however, that the machine tool accumulator charging unit 84a and/or the charging unit 86a for charging the external unit 58a are/is designed as a contact charging unit.

In addition, the storage system 10a comprises at least one communication device 60a at least for exchanging electronic data with the work clothing 14a. The communication device 60a is provided for a wireless exchange of electronic data with the work clothing 14a. In this case, electronic data can be exchanged between the work clothing 14a and the external unit 58a by means of the communication device 60a. In addition, electronic data which define a usage duration and/or a degradation of the work clothing 14a can be exchanged by means of the communication device 60a, wherein the usage duration and/or the degradation can be sensed by at least the sensor unit 62a of the work clothing 14a and/or by the sensor device 28a. Furthermore, electronic data which define a user-specific characteristic variable of a wearer of the work clothing 14a can be exchanged by means of the communication device 60a, wherein the user-specific characteristic variable can be sensed by at least the sensor unit 62a of the work clothing 14a.

The storage system 10a also comprises at least one control and/or regulating device 64a which is provided for setting at least one characteristic variable of the work clothing 14a depending on an individualized user input and/or depending on electronic data exchanged by means of the communication device 60a. An individualized adaptation of the work clothing 14a to a wearer and/or a place of use can therefore take place, in particular at least partially semi-automatically.

Furthermore, the storage system 10a comprises at least one drying and/or cleaning device 66a which is provided for carrying out a drying and/or cleaning process of the work clothing 14a depending on at least one characteristic variable sensed by means of the sensor device 28a and/or depending on electronic data exchanged by means of the communication device 60a. In this case, it is conceivable that the sensor unit 62a of the work clothing 14a comprises at least one moisture sensor element (not shown here in greater detail), by means of which a characteristic variable designed as moisture of the work clothing 14a can be sensed, which characteristic variable can be transmitted to the storage system 10a by means of the communication device 60a, wherein a drying and/or cleaning process can be carried out depending on a value of the characteristic variable designed as moisture of the work clothing 14a. It is also conceivable that the drying and/or cleaning process can be carried out depending on a desire of a wearer of the work clothing 14a, which is entered by means of an input device 88a of the storage system 10a. Further processes for carrying out a drying and/or cleaning process, which appear reasonable to a person skilled in the art, are also conceivable, such as, for example, as a result of a communication by an external unit 58a with the storage system 10a by means of the communication device 60a, or the like. The input device 88a can also be provided for an actuation of a locking unit of the storage device 12a.

In addition, the storage system 10a comprises at least one output device 68a for outputting information at least regarding a state of the work clothing 14a. The output device 68a in this case can be designed as an optical, haptic and/or acoustic output device. It is also conceivable that the output device 68a is designed at least partially as one piece with the input device 88a, in particular in an embodiment of the input device 88a as a touch-sensitive display device. The output device 68a is at least provided for outputting a status of a charging process of the charging device 16a and a charge status of the energy storage units 18a, 20a, 22a, 24a, 26a of the work clothing 14a and of the machine tool accumulator device 56a and an energy storage unit of an external unit 58a, in particular in a state of the work clothing 14a disposed on the charging device 16a and/or on the storage device 12a, and of the machine tool accumulator device 56a and of the external unit 58a. In this case, the output device 68a comprises output elements which are disposed on the corresponding charging units of the charging device 16a. In addition, the output device 68a is provided for outputting a status of the storage device 12a, such as, for example, a closure status, a drying and/or cleaning status, a status regarding which work-clothing items 30a, 32a, 34a, 36a, 38a of the work clothing 14a are disposed on the storage device 12a, or the like. For this purpose, at least one optical element, in particular a lighting element, such as, for example, an LED or a lamp, etc., of the output device 68a is disposed on an outer side of the storage device 12a. In addition, a touch-sensitive display device of the output device 68a, which at least partially forms the input device 88a, is disposed on the storage device 12a on an inner side, in particular on an inner side of the closure element 70a. Further output elements of the output device 68a, which appear reasonable to a person skilled in the art, are also conceivable, wherein a person skilled in the art will arrange the further output elements in a way which appears reasonable to him.

Figure 8:
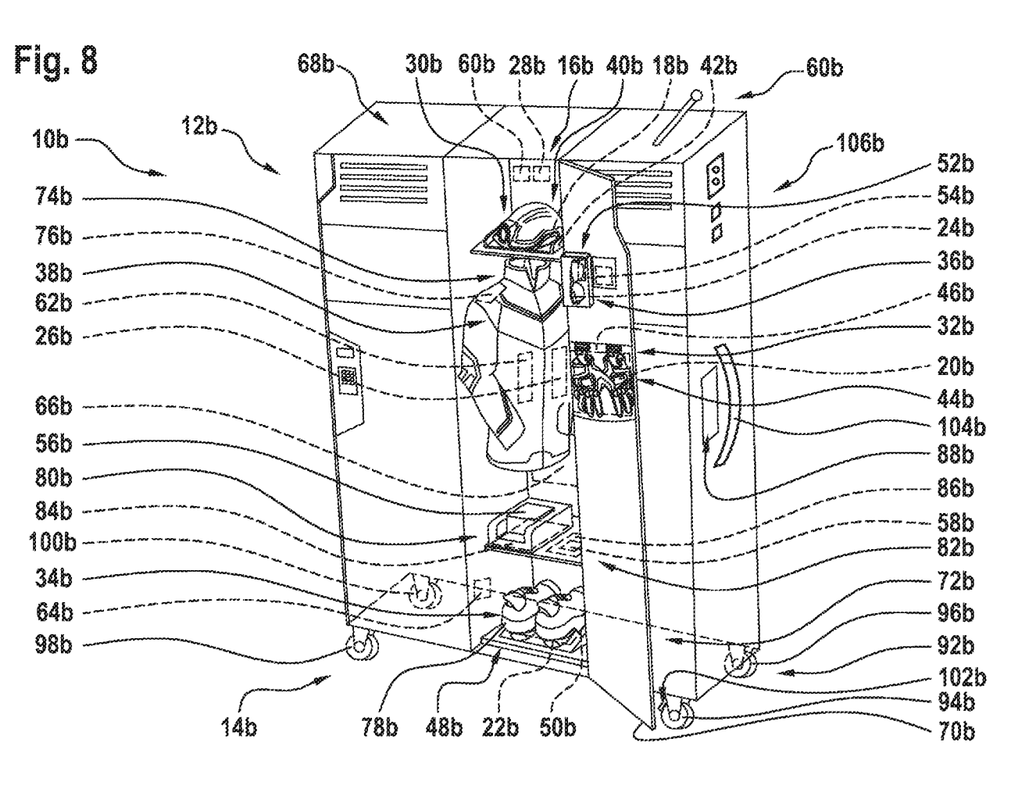
FIG. 8 shows a schematic representation of an alternative storage system according to the disclosure.
Figure 9:
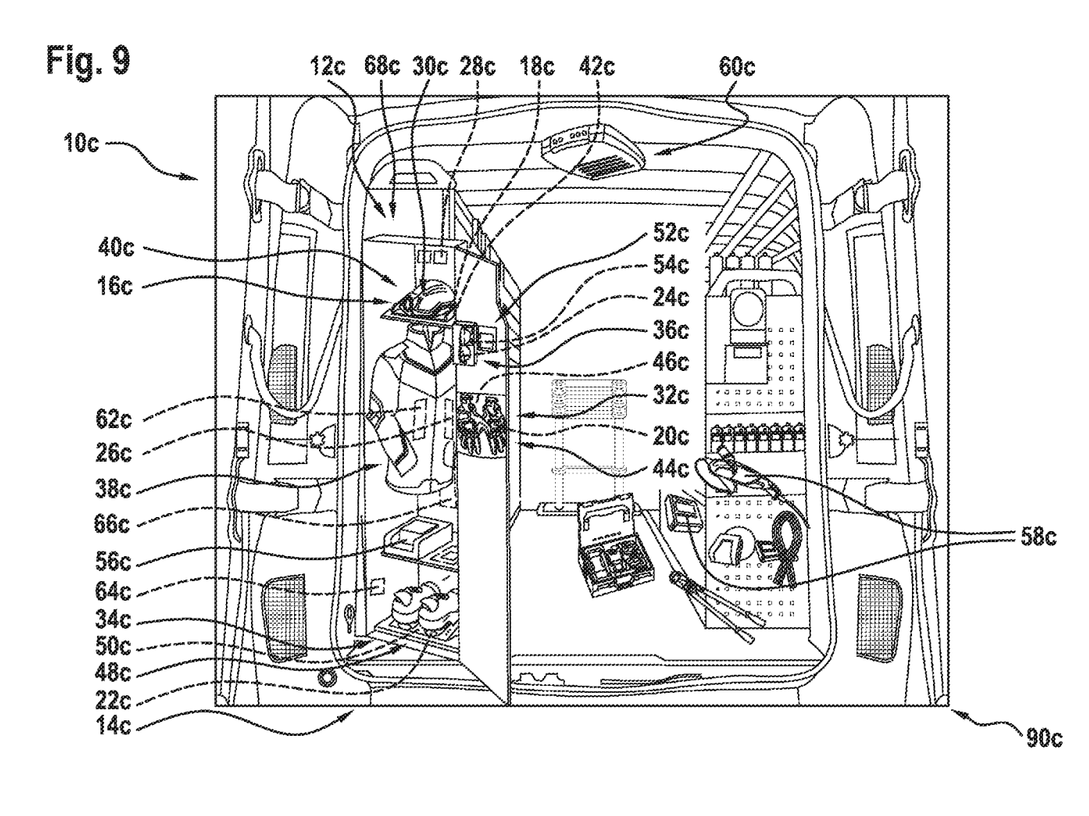
FIG. 9 shows a schematic representation of a further, alternative storage system according to the disclosure.

Further exemplary embodiments of the disclosure are shown in FIGS. 8 and 9. The following descriptions and the drawing are essentially limited to the differences between the exemplary embodiments, wherein, in principle, reference can also be made to the drawing and/or the description of the other exemplary embodiments, in particular of FIGS. 1 to 7, with respect to identically designated components, in particular with respect to components having the same reference numbers. For the purpose of differentiating the exemplary embodiments, the letter "a" is placed after the reference number of the exemplary embodiment in FIGS. 1 to 7. In the exemplary embodiments of FIGS. 8 and 9, the letter "a" is replaced by the letters "b" and "c".

FIG. 8 shows an alternative storage system 10b which comprises at least one storage device 12b at least for storing work clothing 14b, at least one wired and/or wireless charging device 16b which is provided for transmitting at least electrical energy to at least one energy storage unit 18b, 20b, 22b, 24b, 26b of the work clothing 14b, and at least one sensor device 28b at least for sensing at least one characteristic variable of the work clothing 14b. The charging device 16b is provided, in this case, for charging different work-clothing items 30b, 32b, 34b, 36b, 38b of the work clothing 14b, which can be disposed on the storage device 12b. As compared to the storage device 12a described in the description of FIGS. 1 to 7, the storage device 12b represented in FIG. 8 is designed to be mobile. In this case, the storage device 12b comprises at least one mobility unit 92b. In this case, the mobility unit 92b comprises at least one roller 94b, by means of which the storage device 12b can be moved. In all, the mobility unit 92b comprises four rollers 94b, 96b, 98b, 100b. In this case, one roller 94b, 96b, 98b, 100b of the rollers 94b, 96b, 98b, 100b is disposed at each of the edge areas, in particular at a corner, of the storage device 12b. The mobility unit 92b further comprises at least one brake unit 102b for blocking a mobility of at least one of the rollers 94b, 96b, 98b, 100b. The brake unit 102b is designed as a friction brake unit in this case, which comprises at least one brake element (not shown here in greater detail) designed as a brake pad. Furthermore, the mobility unit 92b comprises at least one handle 104b. Alternatively or additionally, it is conceivable that the mobility unit 92b comprises at least one drive unit, by means of which the storage device 12b can be moved at least partially automatically. Therefore, it is conceivable that the storage device 12b is designed to be remote-controllable, similarly to a RC model. Further embodiments of the mobility unit 92b, which appear reasonable to a person skilled in the art, are also conceivable. All further devices and units of the storage system 10b are disposed on the storage device 12b or are integrated therein in this case, as already described in the description of FIGS. 1 to 7. In order to supply the charging device 16b with electrical energy, the storage system 10b comprises at least one energy connection device 106b. The energy connection device 106b in this case has a design which is already known to a person skilled in the art. With respect to further functions and features of the storage system 10b represented in FIG. 8, reference may be made to the storage system 10a represented in FIGS. 1 to 7.

FIG. 9 shows a further alternative storage system 10c which comprises at least one storage device 12c at least for storing work clothing 14c, at least one wired and/or wireless charging device 16c which is provided for transmitting at least electrical energy to at least one energy storage unit 18c, 20c, 22c, 24c, 26c of the work clothing 14c, and at least one sensor device 28c at least for sensing at least one characteristic variable of the work clothing 14c. The charging device 16c is provided, in this case, for charging different work-clothing items 30c, 32c, 34c, 36c, 38c of the work clothing 14c, which can be disposed on the storage device 12c. As compared to the storage device 12a described in the description of FIGS. 1 to 7, the storage device 12c represented in FIG. 9 is integrated into a mobile unit 90c. The mobile unit 90c is designed as a commercial vehicle in this case. It is also conceivable, however, that the mobile unit 90c has another design which appears reasonable to a person skilled in the art, such as, for example, a passenger vehicle, a truck, or the like. In this case, all further devices and units of the storage system 10c can be disposed on the storage device 12c, integrated therein, or individually integrated into the mobile unit 90c. With respect to further functions and features of the storage system 10c represented in FIG. 8, reference may be made to the storage system 10a represented in FIGS. 1 to 7.

The invention claimed is:

1. A storage system comprising:
    at least one storage device configured to store work clothing;
    at least one wired and/or wireless charging device configured to transmit electrical energy to at least one energy storage unit of the work clothing;
    at least one sensor device configured to sense at least one characteristic variable of the work clothing;
    at least one communication device configured to exchange electronic data with the work clothing; and
    at least one drying and/or cleaning device configured to carry out at least one of (i) a drying process and (ii) a cleaning process of the work clothing depending on at least one of (i) at least one characteristic variable and (ii) electronic data exchanged using the at least one communication device, wherein
    the at least one sensor device is configured to sense the at least one characteristic variable, and
    the at least one wired and/or wireless charging device is further configured to charge different work-clothing items of the work clothing, the work clothing being configured to be disposed on the at least one storage device.

2. The storage system as claimed in claim 1, wherein the at least one storage device includes at least one safety helmet storage unit,
    wherein at least one work-clothing item of the work-clothing items of the work clothing is operable as a safety helmet and is configured to be disposed in the at least one safety helmet storage unit, and
    wherein at least one safety helmet charging unit of the at least one wired and/or wireless charging device is disposed on the safety helmet storage unit and is configured to charge at least one energy storage unit of the safety helmet.

3. The storage system as claimed in claim 1, wherein the at least one storage device includes at least one glove storage unit,
    wherein at least one work-clothing item of the work-clothing items of the work clothing is operable as a pair of gloves and is configured to be disposed in the at least one glove storage unit, and
    wherein at least one glove charging unit of the at least one wired and/or wireless charging device is disposed on the glove storage unit and is configured to charge at least one energy storage unit of the pair of gloves.

4. The storage system as claimed in claim 1, wherein the at least one storage device includes at least one work shoe storage unit,
    wherein at least one work-clothing item of the work-clothing items of the work clothing operable as a pair of work shoes and is configured to be disposed in the at least one work shoe storage unit, and
    wherein at least one work shoe charging unit of the at least one wired and/or wireless charging device is disposed on the work shoe storage unit and is configured to charge at least one energy storage unit of the pair of work shoes.

5. The storage system as claimed in claim 1, wherein the at least one storage device includes at least one safety glasses storage unit,
    wherein at least one work-clothing item of the work-clothing items of the work clothing is operable as safety glasses and is configured to be disposed in the at least safety glass storage unit, and
    wherein at least one safety glasses charging unit of the at least one wired and/or wireless charging device is disposed on the safety glasses storage unit and is configured to charge at least one energy storage unit of the safety glasses.

6. The storage system as claimed in claim 1, wherein the at least one wired and/or wireless charging device is further configured to charge at least one of (i) at least one machine tool accumulator device and (ii) at least one energy storage unit of an external unit.

7. The storage system as claimed in claim 1, wherein the at least one communication device is further configured to exchange electronic data between the work clothing and an external unit.

8. The storage system as claimed in claim 1, wherein the at least one communication device is further configured to exchange electronic data,
    wherein the electronic data includes at least one of (i) a usage duration and (ii) a degradation of the work clothing, and
    wherein at least one of (i) at least one sensor unit of the work clothing and (ii) the sensor device is configured to sense the at least one of (i) the usage duration and (ii) the degradation.

9. The storage system as claimed in claim 1, wherein the at least one communication device is further configured to exchange electronic data,
    wherein the electronic data includes a user-specific characteristic variable of a wearer of the work clothing, and
    wherein at least one sensor unit of the work clothing is configured to sense the user-specific characteristic variable.

10. The storage system as claimed in claim 1, further comprising:
    at least one control and/or regulating device configured to set at least one characteristic variable of the work clothing depending on at least one of (i) an individualized user input and (ii) electronic data exchanged using the at least one communication device.

11. The storage system as claimed in claim 1, further comprising:
    at least one output device configured to output information regarding a state of the work clothing.

12. The storage system as claimed in claim 1, wherein at least the storage device is further configured to be mobile or is further configured to be integrated in a mobile unit.

13. The storage system as claimed in claim 1, wherein the storage system is a work-clothing storage system.

* * * * *